US007681811B2

(12) United States Patent
Geser et al.

(10) Patent No.: US 7,681,811 B2
(45) **Date of Patent: *Mar. 23, 2010**

(54) SYSTEM COMPRISING A NOZZLE AND A FIXING MEANS THEREFOR

(75) Inventors: Johannes Geser, Ingelheim (DE); Dieter Hochrainer, Schmallenberg (DE); Herbert Wachtel, Ingelheim (DE); Stephen Dunne, Suffolk (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 64 days.

This patent is subject to a terminal disclaimer.

(21) Appl. No.: 11/764,248

(22) Filed: Jun. 18, 2007

(65) Prior Publication Data

US 2007/0257134 A1 Nov. 8, 2007

Related U.S. Application Data

(63) Continuation of application No. 10/982,991, filed on Nov. 5, 2004, now Pat. No. 7,284,713, which is a continuation of application No. 10/429,500, filed on May 2, 2003, now abandoned.

(60) Provisional application No. 60/382,129, filed on May 21, 2002.

(30) Foreign Application Priority Data

May 16, 2002 (DE) ................................ 102 21 732

(51) Int. Cl.
*A62C 2/08* (2006.01)

(52) U.S. Cl. ...................................... 239/548; 239/589

(58) Field of Classification Search ................ 239/548, 239/396, 397, 422, 428, 433, 290, 91, 418, 239/419, 589, 291
See application file for complete search history.

(56) References Cited

U.S. PATENT DOCUMENTS

| | | | |
|---|---|---|---|
| 3,769,037 A | 10/1973 | Sholl | |
| 4,258,885 A * | 3/1981 | Legeza | 239/707 |
| 4,300,723 A | 11/1981 | Prasthofer | |
| 4,623,337 A | 11/1986 | Maurice | |
| 4,765,540 A | 8/1988 | Yie | |

(Continued)

FOREIGN PATENT DOCUMENTS

| | | |
|---|---|---|
| DE | 2358513 | 5/1974 |

(Continued)

*Primary Examiner*—Davis Hwu
(74) *Attorney, Agent, or Firm*—Michael P. Morris; Mary-Ellen M. Devlin; Alan R. Stempel

(57) ABSTRACT

The invention relates to a nozzle system for a delivery device for liquids, wherein the nozzle system comprises a nozzle and a device which fixes the nozzle in the delivery device. The delivery device, an atomizer, has a liquid reservoir from which a liquid is forced through the nozzle under pressure. The nozzle fixing means may itself be secured by a second fixing, e.g., in the form of a check nut, or the fixing may itself be a check nut. According to the invention the fixing means on the nozzle outlet side has a specific geometry which minimizes the proportion of dispensed liquid deposited on the fixing means. Preferably, the present invention is part of a propellant-free device for nebulizing pharmaceutical liquids.

22 Claims, 12 Drawing Sheets

U.S. PATENT DOCUMENTS

| | | | | | |
|---|---|---|---|---|---|
| 5,060,869 | A | | 10/1991 | Bekius | |
| 5,358,179 | A | | 10/1994 | Lund et al. | |
| 5,472,143 | A | | 12/1995 | Bartels et al. | |
| 5,553,783 | A | | 9/1996 | Slavas et al. | |
| 5,565,241 | A | | 10/1996 | Mathias et al. | |
| 5,725,680 | A | | 3/1998 | Mathieus | |
| 5,845,846 | A | * | 12/1998 | Watanabe et al. | 239/8 |
| 5,996,576 | A | | 12/1999 | Yule | |
| 6,085,740 | A | | 7/2000 | Ivri et al. | |
| 6,098,897 | A | | 8/2000 | Lockwood | |
| 6,394,366 | B1 | | 5/2002 | Adams | |
| 6,402,055 | B1 | | 6/2002 | Jaeger et al. | |
| 2002/0193392 | A1 | | 12/2002 | Schmelzer et al. | |

FOREIGN PATENT DOCUMENTS

| | | | |
|---|---|---|---|
| DE | 2408509 | | 9/1975 |
| DE | 19928614 | C1 | 2/2001 |
| GB | 1547799 | | 6/1979 |
| RU | 2024323 | | 12/1994 |
| WO | 9407607 | A1 | 4/1994 |
| WO | 9712687 | A1 | 4/1997 |

* cited by examiner

SYSTEM COMPRISING A NOZZLE AND A FIXING MEANS THEREFOR

CROSS-REFERENCE TO RELATED APPLICATIONS

This is a continuation of U.S. patent application Ser. No. 10/982,991, filed on Nov. 5, 2004, which is a continuation of U.S. patent application Ser. No. 10/429,500, filed on May 2, 2003, now abandoned, which claims the benefit of U.S. Provisional Application Ser. No. 60/382,129, filed on May 21, 2002.

BACKGROUND

The invention relates to a nozzle system for a delivery device for liquids, wherein the nozzle system comprises a nozzle and a device which fixes the nozzle in the delivery device. The delivery device, an atomizer, has a liquid reservoir from which a liquid is forced through the nozzle under pressure. The nozzle fixing means may itself be secured by a second fixing, e.g., in the form of a check nut, or the fixing may itself be a check nut. According to the invention the fixing means on the nozzle outlet side has a specific geometry which minimizes the amount of dispensed liquid deposited on the fixing means.

Preferably, the present invention is part of a propellant-free device for nebulizing pharmaceutical fluids. A nebulizer according to the invention is used, for example, to produce an aerosol of droplets for inhalation through the mouth and pharyngeal cavity into the lungs of a patient, for nasal administration or for spraying the surface of the eye.

WO 91/14468 discloses an apparatus for propellant-free administration of a metered quantity of a liquid pharmaceutical for application by inhalation. A further development of the device is described in detail in WO 97/12687. Reference is specifically made to these publications and the technology described therein is referred to within the scope of the present invention as Respimat™ technology. This term refers in particular to the technology which forms the basis for a device according to FIGS. 6a and 6b of WO 97/12687 and the associated description. Propellant-free liquids can easily be atomized using such devices.

In an inhaler of this kind liquid pharmaceutical formulations are stored in a reservoir. From there, they are conveyed through a riser tube into a pressure chamber from where they are forced through a nozzle.

The nozzle is held by a nozzle holder and the latter is secured by a check nut. The check nut has a liquid inlet side and a liquid outlet side. On the liquid inlet side is an opening through which a liquid from the pressure chamber can enter the nozzle. On the opposite side, the end face of the nozzle, the liquid then passes through two nozzle apertures which are aligned so that the jets of liquid leaving the apertures strike one another and are thereby atomized. The nozzle apertures are arranged in the inhaler in such a way that they are in direct contact with the outer environment.

This is achieved by the fact that the entire region of the nozzle holder and check nut which is located above the nozzle apertures has a recess (or hole or bore) through it which provides a pathway for a jet of liquid leaving the nozzle or an emerging aerosol to leave the atomizer through the mouthpiece.

In the region of this nozzle holder this recess is funnel-shaped while in the region of the check nut this recess is in the form of a uniform cylinder. The transition between the nozzle holder and check nut has a sharp edge so that the cross section of the recess is like an L in which the crossbar is inclined slightly downwards. The entire recess in front of the nozzle aperture, which is made up of the recess in the nozzle holder and the recess of the check nut, has a point of discontinuity in the elbow region of this L: the recess expands discontinuously, i.e., viewed from the base it first of all widens out and then bends sharply vertically in the region of the transition from the nozzle holder to the check nut. The vertical direction corresponds to the direction of spraying of the emerging liquid, i.e., the perpendicular to the outside of the nozzle (end face).

These inhalers normally deliver formulations based on water or mixtures of water and ethanol. They are able to nebulize a small amount of a liquid formulation in the therapeutically required dosage within a few seconds to produce an aerosol suitable for therapeutic inhalation. With the device, quantities of less than 100 microlitres can be nebulized, e.g., with one spray actuation, to produce an aerosol with an average particle size of less than 20 microns so that the inhalable part of the aerosol corresponds to the therapeutically effective amount. In these nebulizers with Respimat™ technology a pharmaceutical solution is converted by high pressure up to 500 bar into a low-speed aerosol mist destined for the lungs, which the patient can then breathe in.

A small amount of the liquid may be deposited from the outside as a film or as an accumulation of small droplets on the end face of the nozzle or on the end face of the fixing means for the nozzle or on the inside of the mouthpiece. This fraction of the liquid is also referred to as the mouthpiece fraction within the scope of this specification. This mouthpiece fraction reduces the amount of liquid dispensed, with the result that the inhalable fraction of the quantity delivered is reduced by the mouthpiece fraction.

The amount of liquid deposited need not be constant in every spray actuation but may depend on numerous factors such as the spatial orientation of the device during the aerosol production or the ambient temperature, relative humidity, etc. This leads on the one hand to a certain variability, however minor, in the amount dispensed which is then available for the patient to take in (delivered dose). Of the delivered dose, some has such a small particle size that the particles can be breathed deep into the lungs and this fraction is known as the inhalable fraction. However, the present specification does not expressly differentiate between the inhalable fraction and the total quantity of aerosol available for the patient to breathe in unless otherwise stated or unless clearly apparent from the context.

The liquid deposited may also cause contamination of the outer surface of the nozzle system or of the mouthpiece, which may in turn affect the pharmaceutical quality of the next aerosol mist.

Although these two effects are only slight in devices using Respimat™ technology it is important for reasons of quality control to minimize such effects.

It has now been found that in devices of this kind for dispensing liquids the proportion of liquid deposited on the outside of the nozzle system can be reduced by the particular geometry of the nozzle or nozzle fixing means. In fact, it has been found, surprisingly, that the mouthpiece fraction can be reduced if the entire area above the nozzle aperture (i.e., the area through which the dispensed liquid "flies" on its way to the mouthpiece) is funnel-shaped and has no edges.

SUMMARY OF THE INVENTION

It is an objective of the invention to reduce the variability of the proportion of the liquid delivered by means of a device for delivering pharmaceutical liquids, such as atomizers, inhalers, etc.

A further aim of the invention is to reduce the proportion of liquid which is deposited, from an aerosol mist, on the device for delivering the pharmaceutical liquid.

Thus, a further aim of the invention is to increase the inhalable fraction of the quantity delivered and to reduce the mouthpiece fraction.

A further aim is to optimize the quality of delivery of a liquid using atomizers having the Respimat™ technology.

This objective is achieved by means of a nozzle system which consists of a nozzle having at least two nozzle apertures and a nozzle holder and optionally a check nut, wherein the nozzle apertures formed on the end face of the nozzle or the nozzle channels opening into the nozzle apertures are arranged so that the jets leaving the nozzle apertures are aimed towards one another at an angle $\alpha$, the nozzle is arranged in the nozzle holder and this is optionally fixed by a check nut located above it, in the assembled state the nozzle holder or the check nut or both extend at least partially into the area in front of the nozzle apertures, and the nozzle system is characterized in that in the assembled state the nozzle holder or, if the nozzle system has a check nut, the nozzle holder together with the check nut has an inner recess, which begins on the side adjacent to the end face of the nozzle and extends as far as the outside of the nozzle holder parallel thereto or, in the case of a check nut, as far as the outside thereof parallel to the end face of the nozzle, which, viewed from the end face of the nozzle, widens out steadily and continuously in the direction of the outside of the nozzle holder parallel thereto or, in the case of a check nut, the outside of said check nut parallel thereto, so that the recess opens up the area of the nozzle system between the end face of the nozzle and the outside of the nozzle holder parallel thereto or, in the case of a check nut, the outside of said check nut parallel thereto, for a liquid emerging from the nozzle opening to pass through, so that this liquid can emerge from the nozzle, unimpeded by the nozzle holder and the check nut, if applicable, and can be distributed in the surrounding area.

According to advantageous embodiments of the nozzle system, the recess is funnel-shaped, preferably conical in construction.

The expression "continuously widening recess" refers within the scope of the present invention to a surface the edge of which runs continuously in cross section. This refers to the area which is macroscopically visible. By "runs continuously" is meant that there are no gaps of more than 0.5 mm, preferably more than 0.1 mm.

In cross section the edge of this "continuously widening recess" is preferably in the form of a straight, elliptical, hyperbolic, convex or concave line. In any case the edge runs continuously. The recess also widens continuously and does not merge into a cylindrical area.

The region of the recess with the smallest diameter, the base point, is located on the side of the nozzle holder which is adjacent to the end face of the nozzle.

The part of the recess with the largest diameter, the apex or vertex, is on the opposite side, i.e., the outside of the nozzle holder parallel to the end face of the nozzle or, in the case of a check nut, the outside of said check nut which is parallel thereto.

The small diameter of the recess is between 0.1 mm and 2 mm, preferably between 0.6 mm and 1.0 mm. The larger diameter of the recess is between 3 mm and 10 mm, preferably between 5 mm and 8 mm.

The transition of the base end of the recess to the end face of the nozzle may be constructed as an edge or it may be continuous, as defined above, i.e., with no edges.

In the system according to the invention a check nut is not necessary if the nozzle holder itself takes on this function.

Preferably, the nozzle system has a check nut. In this case the transition between the nozzle holder and the check nut is constructed with no edges, i.e., the continuous run of the recess is uninterrupted. Preferably, there is no change in the gradient of the preferably conically widening recess in this area.

As an aid to solving the problem posed, it is also possible to vary the spacing of the nozzle aperture and the angle of inclination at which jets of liquid are delivered from the nozzle apertures.

The present invention is based on nozzle systems as described, for example, in EP 0664733 or EP 1017469. These are preferably nozzles consisting of at least two superimposed plates, at least one of the plates having a second microstructure so that the superimposed plates define on one side a liquid inlet adjoining a channel system and/or a filter system which then opens into the liquid outlets.

Microstructured nozzled bodies of this kind are described for example in WO 94/07607 or WO 99/16530. Another embodiment is disclosed in the German Patent application filed under No. 10216101.1. Reference is hereby made to all the documents.

With regard to WO 94/07607 we refer particularly to FIG. 1 and the associated description. The nozzle body consists, for example, of two sheets of glass and/or silicon firmly attached to one another, at least one of these sheets having one or more microstructured channels which connect the nozzle inlet side to the nozzle outlet side. On the nozzle outlet side there may be at least one, preferably, according to the invention, two round or non-round openings 2 to 10 microns deep and 5 to 15 microns wide, the depth preferably being 4.5 to 6.5 microns and the length preferably being 7 to 9 microns.

On the base part, on the flat surface, there may be a set of channels to create a plurality of filter routes (filter channels) in collaboration with the substantially flat surface of the top part. The base part may have a fill chamber the top of which is again formed by the top part. This fill chamber may be provided before or after the filter channels. It is also possible to have two fill chambers of this kind. Another set of channels on the substantially flat surface of the base part which is provided downstream of the filter channels forms, together with the top part, a set of channels which create a plurality of nozzle outlet routes.

Preferably, the overall cross sectional area of the nozzle outlets is 25 to 500 square micrometers. The total cross sectional area is preferably 30 to 200 square micrometers.

In another embodiment this nozzle construction has only one nozzle aperture.

In other embodiments of this kind the filter channels and/or the fill chamber are omitted. Preferably, the filter channels are formed by projections arranged in a zigzag shape. Thus, for example, a zigzag configuration of this kind is formed by at least two rows of projections. A number of rows of projections may also be formed, the projections being laterally offset from one another in order to construct additional rows which are skewed relative to these rows, these additional rows forming the zigzag configuration. In embodiments of this kind the inlet and outlet may each have a longitudinal slot for unfiltered or filtered fluid, each of the slots being substantially the same width as the filter and substantially the same height as the projections on the inlet and outlet sides of the filter. The cross section of the through flow passages formed by the projections may be perpendicular to the direction of flow of the fluid and may decrease from row to row, viewed in the direction of flow. Also, the projections arranged closer to the inlet side of the filter may be larger than the projections arranged closer to the outlet side of the filter. Additionally, the spacing between the base part and top part may taper in the region from the nozzle inlet side to the nozzle outlet side.

The zigzag configuration which is formed by the minimum of two rows of projections has an angle of inclination a of preferably 20 degrees to 250 degrees.

Further details of this nozzle construction may be found in WO 94/07607. We hereby refer specifically to this publication, particularly FIG. 1 and the associated description.

In embodiments of the nozzle having a plurality of nozzle apertures, preferably all of them are formed on a common side. In such cases the nozzle apertures may be oriented so that the jets of liquid emerging from them meet in front of the nozzle aperture. Systems of this kind require nozzles with at least two apertures. Nozzles of this kind are preferred according to the invention.

The nozzle may be embedded in an elastomeric sleeve as described in WO 97/12683. In its simplest form a sleeve of this kind is a ring or member having an opening into which the nozzle can be inserted. This opening surrounds the nozzle block over its entire outer surface, i.e., the surface which is perpendicular to the preferably linear axis formed by the nozzle inlet side and the nozzle outlet side. The sleeve is open at the top and bottom so as not to impede either the supply of liquid to the nozzle inlet side of the nozzle or the delivery of the liquid. This sleeve may in turn be inserted in a second sleeve. The external form of the first sleeve is preferably conical. The opening of the second sleeve is shaped accordingly. The first sleeve may be made of an elastomer.

The nozzle is secured by the device according to the invention. A nozzle of this kind, optionally including the sleeve, is part of a nozzle system by means of which the nozzle is held at a defined place in the delivery device, preferably from outside in the direction of the hollow piston. According to the invention a nozzle system of this kind therefore consists of a nozzle and a nozzle holder and optionally a check nut. All the elements have an end face. This is the side which is oriented away from the side of the nozzle having the nozzle aperture, i.e., it faces outwards. The inside of the end face of the nozzle holder or the check nut may come into contact with the liquid outlet side of the nozzle and thereby exert the force needed to secure the nozzle in the direction of the liquid inlet side of the nozzle. The end face of the nozzle holder and/or of the check nut has or have a through-bore or hole in the form of a recess through which the aerosol can escape from the nozzle. Therefore, the nozzle apertures are in, or in a direct line below, the bore or the recess.

The recess is preferably constructed as an inner recess which widens continuously from the nozzle apertures. Embodiments of the nozzle system wherein the recess is funnel-shaped, preferably conical, are advantageous.

In nozzles having at least two nozzle apertures orientated so that the two jets of liquid leaving the nozzle body meet, the point of impact, the point where the jets of liquid meet and are atomized to form an aerosol, is preferably located close to the base of the recess, i.e., in the region of the nozzle aperture. It is obvious that in such a case the recess is one of the areas particularly at risk of liquid being deposited thereon.

This invention is preferably used in a nebulizer of Respimat™ technology, which is described in more detail hereinafter.

The preferred atomizer essentially comprises a lower and an upper housing mounted to be rotatable relative to one another, the upper part of the housing containing a spring housing with spring which is tensioned by rotating the two housing parts by means of a locking clamping mechanism preferably in the form of a screw thread or gear and is released by pressing a release button on the upper part of the housing. This moves a power take-off flange connected to a hollow piston on the lower end of which a container can be fitted and at the upper end of which are found a valve and a pressure chamber which is connected for fluid transmission to the nozzle or the nozzle system formed in the upwardly open part of the upper housing part. The liquid is sucked in by the hollow piston and pumped to the pressure chamber from where it is expelled through the nozzle in the form of an aerosol.

The hollow piston with valve body corresponds to a device disclosed in WO 97/12687. It projects partially into the cylinder of the pump housing and is disposed to be axially movable in the cylinder. Reference is made particularly to FIGS. 1-4—especially FIG. 3—and the associated parts of the description. At the moment of release of the spring the hollow piston with valve body exerts, at its high pressure end, a pressure of 5 to 60 Mpa (about 50 to 600 bar), preferably 10 to 60 Mpa (about 100 to 600 bar) on the fluid, the measured amount of active substance solution.

The valve body is preferably mounted at the end of the hollow piston which faces the nozzle body. The valve body is connected for fluid transmission with the nozzle. The delivery device also comprises a locking clamping mechanism. This contains a spring, preferably a cylindrical helical compression spring, as a store for the mechanical energy. The spring acts on the power take-off flange as a spring member the movement of which is determined by the position of a locking member. The travel of the power take-off flange is precisely limited by an upper stop and a lower stop. The spring is preferably tensioned via a stepping-up gear, e.g., a helical sliding gear, by an external torque which is generated when the upper housing part is turned relative to the spring housing in the lower housing part. In this case, the upper housing part and the power take-off flange contain a single- or multi-speed spline gear.

The locking member with the engaging locking surfaces is arranged in an annular configuration around the power take-off flange. It consists for example of a ring of plastics or metal which is inherently radially elastically deformable. The ring is arranged in a plane perpendicular to the axis of the atomizer. After the tensioning of the spring, the locking surfaces of the locking member slide into the path of the power take-off flange and prevent the spring from being released. The locking member is actuated by means of a button. The actuating button is connected or coupled to the locking member. In order to actuate the locking clamping mechanism the actuating button is moved parallel to the annular plane, preferably into the atomizer, and the deformable ring is thereby deformed in the annular plane. Details of the construction of the locking clamping mechanism are described in WO 97/20590.

The lower housing part is pushed axially over the spring housing and covers the bearing, the drive for the spindle and the storage container for the fluid.

When the atomizer is operated, the upper part of the housing is rotated relative to the lower part, the lower part taking the spring housing with it. The spring meanwhile is compressed and biased by means of the helical sliding gear, and the clamping mechanism engages automatically. The angle of rotation is preferably a whole-number fraction of 360 degrees, e.g., 180 degrees. At the same time as the spring is tensioned, the power take-off component in the upper housing part is moved along by a given amount, the hollow piston is pulled back inside the cylinder in the pump housing, as a result of which some of the fluid from the storage container is sucked into the high pressure chamber in front of the nozzle.

If desired, a plurality of replaceable storage containers containing the fluid to be atomized can be inserted in the atomizer one after another and then used. The storage container contains the propellant-free aerosol preparation.

The atomizing process is initiated by gently pressing the actuating button. The clamping mechanism then opens the way for the power take-off component. The biased spring pushes the piston into the cylinder in the pump housing. The fluid emerges from the nozzle of the atomizer in the form of a spray. The liquid pharmaceutical preparation hits the nozzle body at an entry pressure of up to 600 bar, preferably 200 to 300 bar and is atomized through the nozzle openings into an inhalable aerosol. The preferred particle sizes of the aerosol are up to 20 microns, preferably 3 to 10 microns. Volumes of 10 to 50 microlitres are preferably delivered, volumes of 10 to 20 microlitres are more preferable, whilst a volume of 15 microlitres per spray is particularly preferred.

The components of the atomizer (nebulizer) consist of a material which is suited to its purpose. The housing of the atomizer and—insofar as the operation allows—other parts are also preferably made of plastics, e.g., by injection molding. For medical uses, physiologically harmless materials are used.

Preferably, a nebulizer according to the invention is cylindrical in shape and has a handy size of less than 9 to 15 cm long and 2 to 4 cm wide, so that it can be carried anywhere by the patient.

Further details of construction are disclosed in PCT applications WO 97/12683 and WO 97/20590, to which reference is made hereby.

The invention is hereinafter illustrated in more detail with reference to drawings.

DETAILED DESCRIPTION OF THE INVENTION

Figure 1:
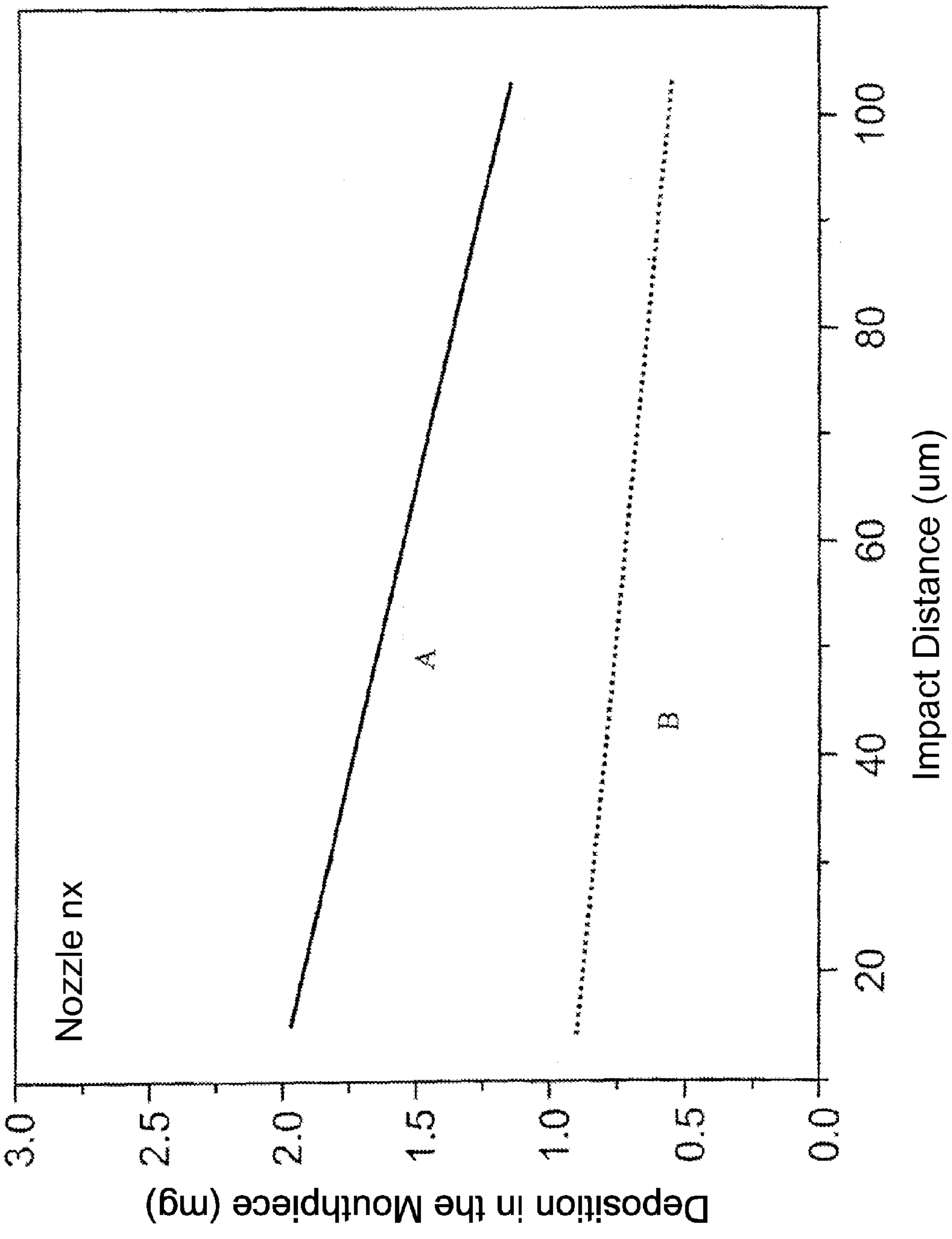
FIG. 1: A graph for investigating nozzle systems with two nozzle apertures directed towards one another: dependency of the mouthpiece fraction ("deposition in the mouthpiece") on the impact height h for a nozzle system with a discontinuously expanding recess and for a nozzle system according to the invention with a conical recess.

FIG. 1 shows the dependency of the mouthpiece fraction ("deposition in the mouthpiece") on the height of impact h for a nozzle system with a discontinuously expanding recess (A) and for a nozzle system according to the invention with a conical recess (B). This graph shows the dependency of the mouthpiece fraction on the height of impact. Accordingly, the mouthpiece fraction can be reduced by increasing the height of impact h.

FIG. 1 also shows that the special construction of the nozzle system according to the invention in the region in front of the nozzle apertures leads to a substantial reduction in the mouthpiece fraction compared with conventional systems. Thus, for example, the mouthpiece fraction can be reduced from about 1.9 mg to 0.8 mg at an impact height h=25 um, corresponding to a reduction of about 60%.

The reduction in the mouthpiece fraction has two positive effects. On the one hand, by minimizing the amount of mouthpiece fraction the quantity delivered is maximized, which in turn has a favorable effect on the inhalable fraction which consequently becomes larger, in principle. This therefore crucially contributes to the solution to one of the problems of the invention, namely of maximizing the inhalable fraction.

Moreover, by reducing the mouthpiece fraction the effects of variability of the mouthpiece fraction are reduced. Because of the small amount of mouthpiece fraction fluctuations in this amount result in only minor fluctuations in the quantity delivered and hence in the inhalable fraction. The inhalable fraction is now highly reproducible, i.e., it has low variability. The problem of the inconstant mouthpiece fraction subject to certain tolerances is now of only marginal importance. This also solves the second problem on which the invention is based, namely of ensuring high reproducibility, i.e., low variability, of the inhalable fraction.

However, what is crucial to the success of the nozzle system according to the invention is that this single measure not only minimizes the mouthpiece fraction but at the same time maximizes the inhalable fraction.

Figure 2:
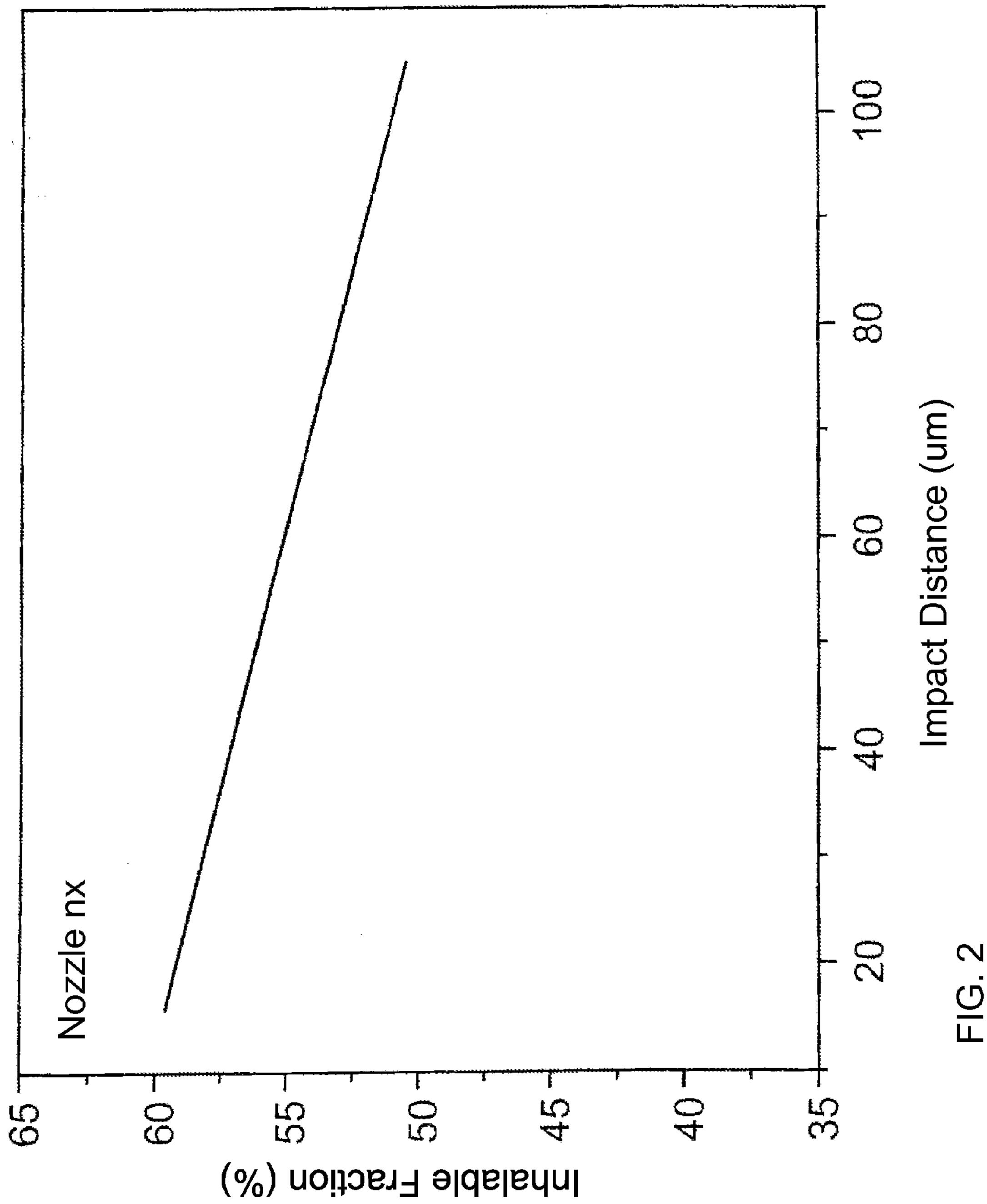
FIG. 2: A graph for investigating nozzle systems with two nozzle apertures directed towards each other: dependency of the aerosol quality on the height of impact.

It is found according to the invention that when reducing the mouthpiece fraction in nozzle systems comprising nozzles with two nozzle apertures aligned so that the jets which emerge from them meet at a point in front of the nozzle (point of impact), it is pointless to increase the height of impact h on its own (FIG. 1). This is because the two jets actually have to meet, which requires the smallest possible height of impact h. Moreover, the jets are supposed to meet in concentrated form before they fall as droplets. In addition it has surprisingly been found that the magnitude of the height of impact h also affects the quality of atomization and hence the inhalable fraction so that, as the height of impact h increases, the quality of atomization or the inhalable fraction is reduced. Then, as the height of impact h increases, there are a greater number of larger particles and fewer small particles. This effect is illustrated in FIG. 2 in which the inhalable fraction is seen as the part which comprises particles with a diameter of less than 5.8 um Here again, the advantageous effect of the nozzle system according to the invention as against a nozzle system with a discontinuously expanding recess is apparent.

Figure 3:
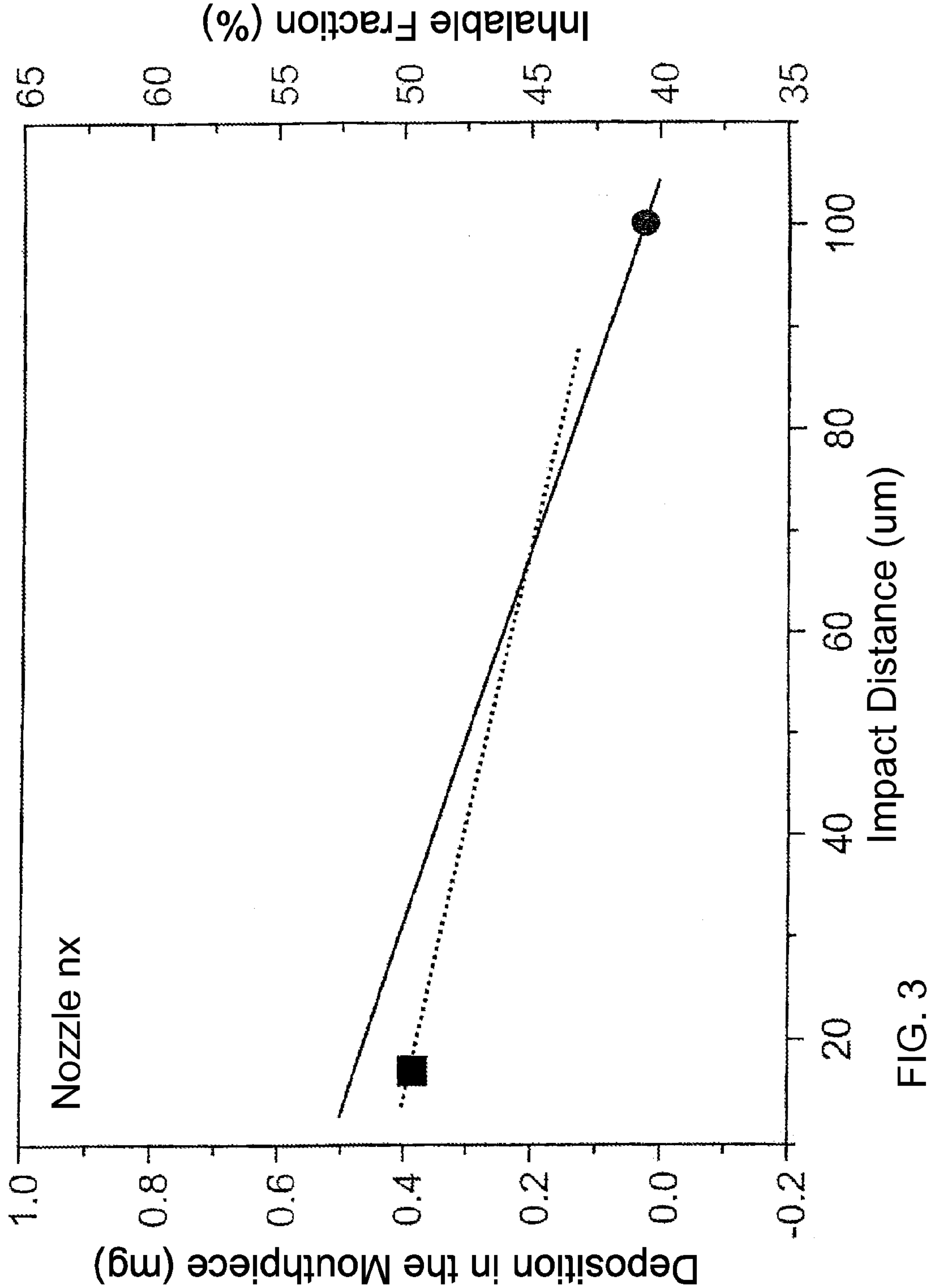
FIG. 3: A graph for investigating nozzle systems with two nozzle openings directed towards one another: dependency of the mouthpiece fraction and the quality of the inhalable fraction on the height of impact.

FIG. 3 shows the mouthpiece fraction in milligrams and the inhalable fraction in percent by volume (proportion by volume of the aerosol containing particles with diameters of less than 5.8 um, as detected by a laser beam) as a function of the height of impact h. For example, for an impact angle $\alpha$=75 degrees the mouthpiece fraction decreases rapidly as the height of impact h increases. At the same time, however, the inhalable fraction, i.e., the quality of atomization, is not reduced to the same extent.

If it is also remembered that not only is the quality of atomization—as characterized by the inhalable fraction in percent by volume—positively affected but also the amount actually delivered is increased by reducing the absolute quantity of the mouthpiece fraction, it will be apparent that the absolute inhalable fraction can be increased substantially.

It has been found according to the invention that in advantageous embodiments of the nozzle system the recesses in front of the nozzle aperture are conical and have a cone angle 2θ in the range between 55 degrees and 155 degrees, preferably in the range between 70 degrees and 140 degrees. Particularly favorable are nozzle systems wherein the recess of conical construction has a cone angle 2θ which is in the range between 70 degrees and 85 degrees or in the range between 95 degrees and 140 degrees, especially in the range between 105 degrees and 125 degrees.

Figure 4:
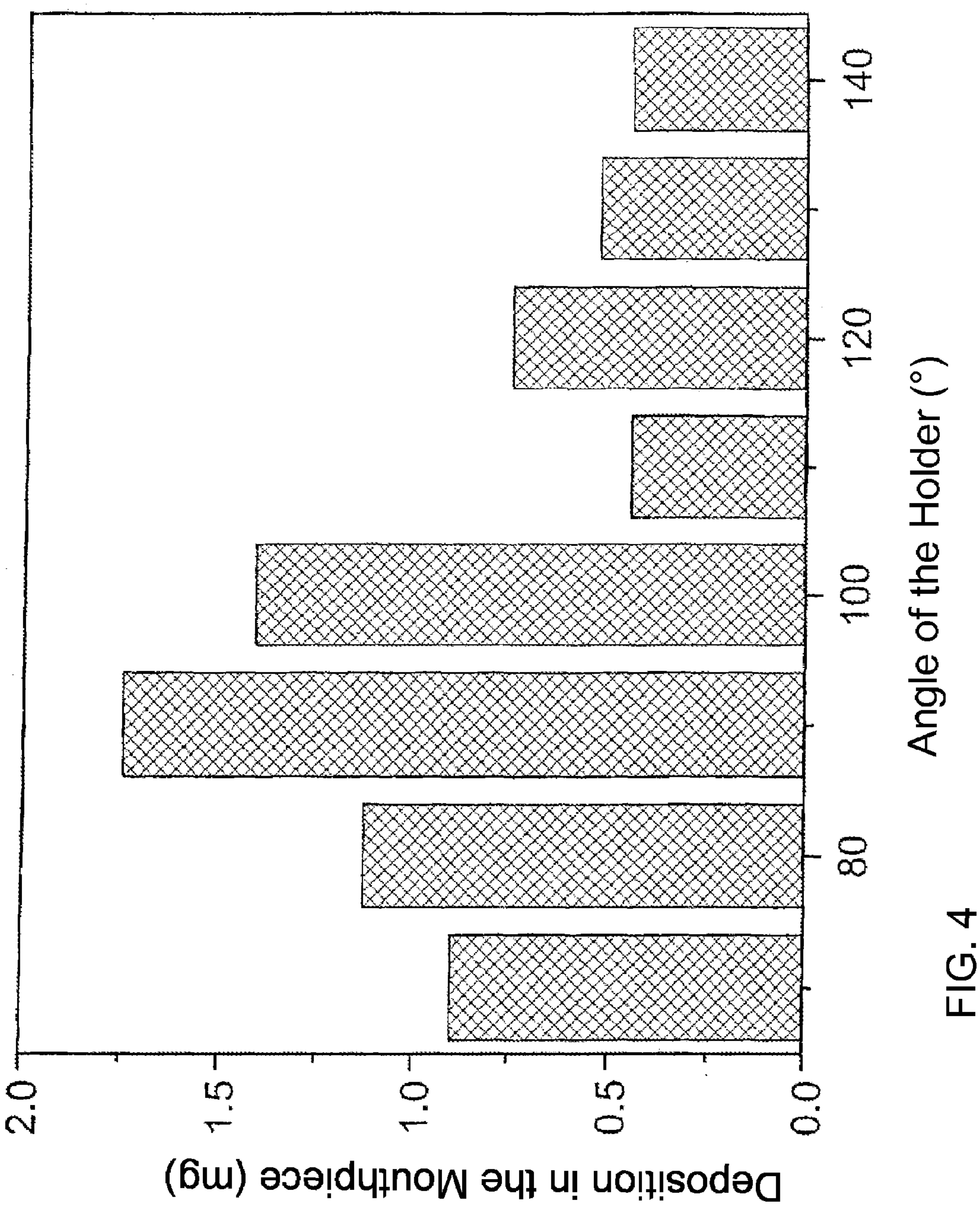
FIG. 4: A graph for investigating nozzle systems with two nozzle apertures directed towards one another: dependency of the mouthpiece fraction on the cone angle 2θ nozzle fixing systems with a conical recess.

The advantages of these embodiments will become apparent from FIG. 4 which shows, in the form of a bar graph, the mouthpiece fraction in milligrams for different cone angles 2θ. All of the embodiments have a mouthpiece fraction of not more than 1.75 mg which is small compared with the prior art (cone angle 2θ=90 degrees). The embodiments which have cone angles 2θ in the range from 70 degrees to 85 degrees or in the range between 95 degrees and 140 degrees, particularly in the range between 105 degrees and 125 degrees, have even smaller mouthpiece fractions. The minimum is obtained with a cone angle 2θ=110 degrees.

According to another aspect the present invention relates to particular nozzles which may advantageously be incorporated in the nozzle systems according to the invention. These nozzles are characterized in that the point of collision where the jets meet has a height of impact h above the nozzle apertures in the range between 20 um and 85 um, preferably in the range between 25 um and 75 um If the height of impact is within the range specified, the various objectives can all advantageously be met, by achieving in particular a low mouthpiece fraction and reliable steering of the jets of liquid towards one another whilst obtaining a high inhalable fraction.

Nozzles wherein the point of collision where the jets meet has a height of impact h above the nozzle apertures in the range between 35 um and 75 um are advantageous. With the impact height in this range the parameters which influence one another are brought to an optimum level.

Embodiments of the nozzles wherein the angle $\alpha$ (is in the range from 50 degrees to 110 degrees, preferably from 65 degrees to 95 degrees and more particularly in the range from 75 degrees to 90 degrees are advantageous.

Figure 5:
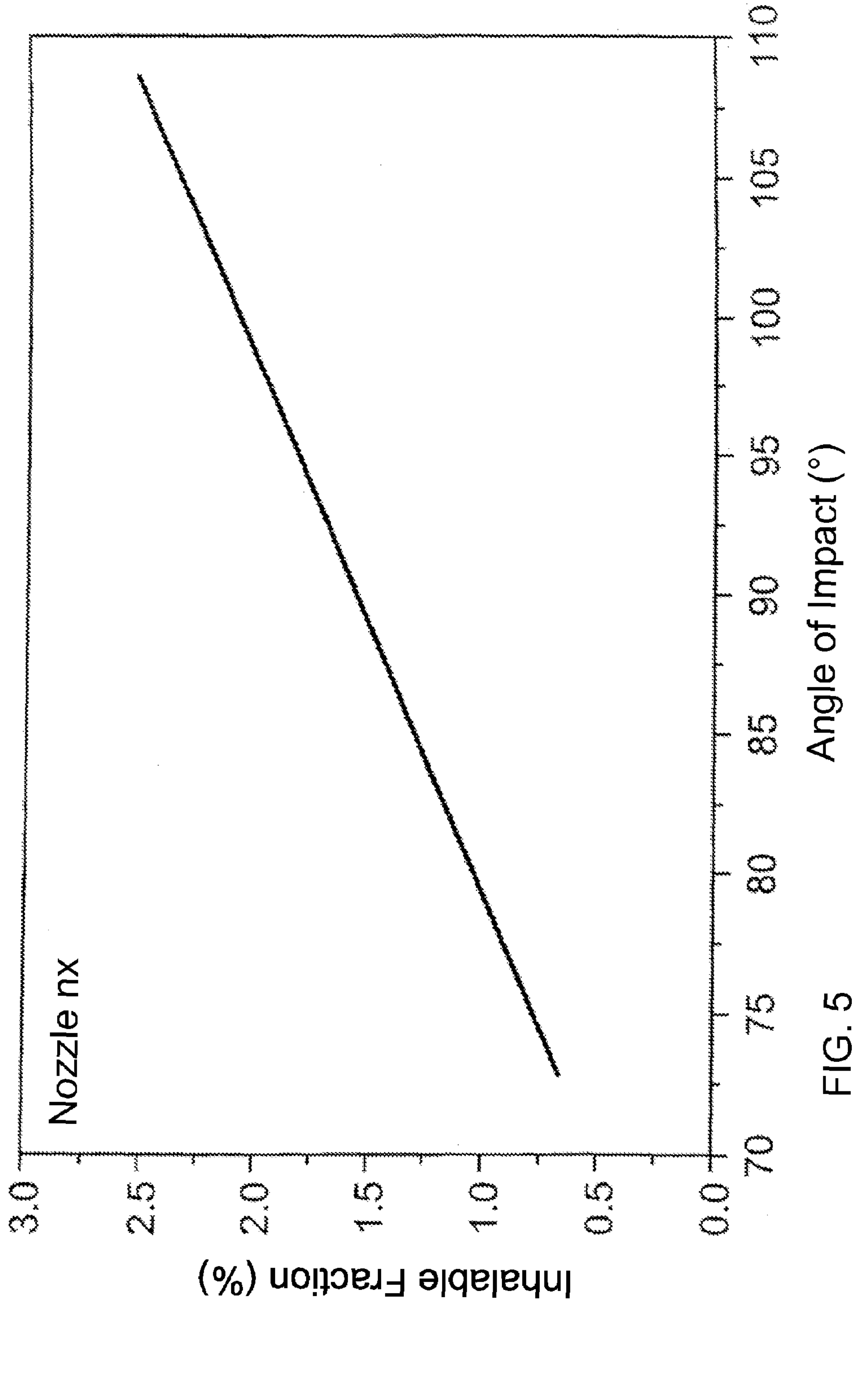
FIGS. 5 and 6: Nozzles with two nozzle apertures directed towards one another: influence of the angle of impact a on the inhalable fraction and the mouthpiece fraction in nozzle fixing systems with a conical recess.
Figure 6:
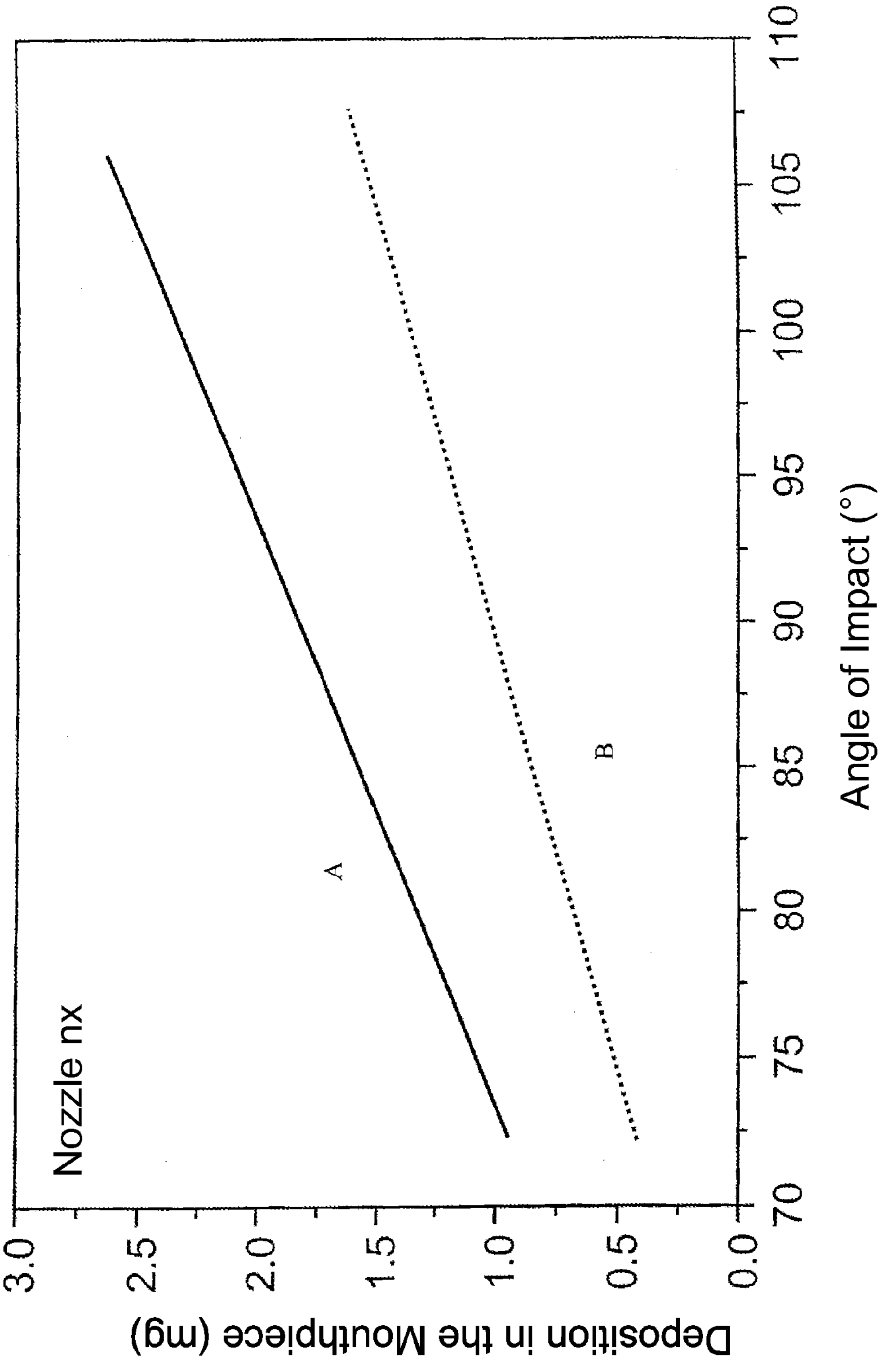

FIGS. 5 and 6 show the effect of the angle of impact a on the inhalable fraction and the mouthpiece fraction. Both these fractions increase as the angle of impact a increases. With regard to the quality of atomization it is preferable for the jets to meet head-on if possible. Large angles ensure a high inhalable fraction, i.e., a high volume proportion of small particles with diameters less than 5.8 um in the spray mist.

However, large angles a also lead to large mouthpiece fractions at the same time. The free path along which the jets travel between leaving the nozzle apertures and meeting one another should not be too great, to ensure among other things that the jets do not disperse before the meeting point. If, however, the angle of impact a is increased, the height of impact must be reduced to keep the free path of the jets constant. The effects of this measure have already been explained. However, even with a constant height of impact and enlargement of the angle, an increasing mouthpiece fraction is obtained as the particles of the spray mist are increasingly driven towards the nozzle system as the angle of impact increases, eventually resulting in a larger mouthpiece fraction. The angle regions mentioned above are best able to accommodate the competing mechanisms.

In advantageous embodiments of the nozzles according to the invention, the spacing a of the nozzle apertures is in the range from 40 um to 125 um, preferably in the range from 50 um to 115 um, more particularly in the range from 60 um to 105 um.

Advantageous embodiments of the nozzle system are characterized in that only the nozzle holder extends into the area in front of the nozzle apertures in the assembled state. This avoids any joints between the nozzle holder and check nut in the region of the nozzle apertures. Joints are a particular problem in terms of the accumulation of aerosol particles as, once deposited, any particles here are not generally released again.

Two embodiments shown in FIGS. 7, 8, 9 and 10 illustrate the invention in more detail.

Figure 7:
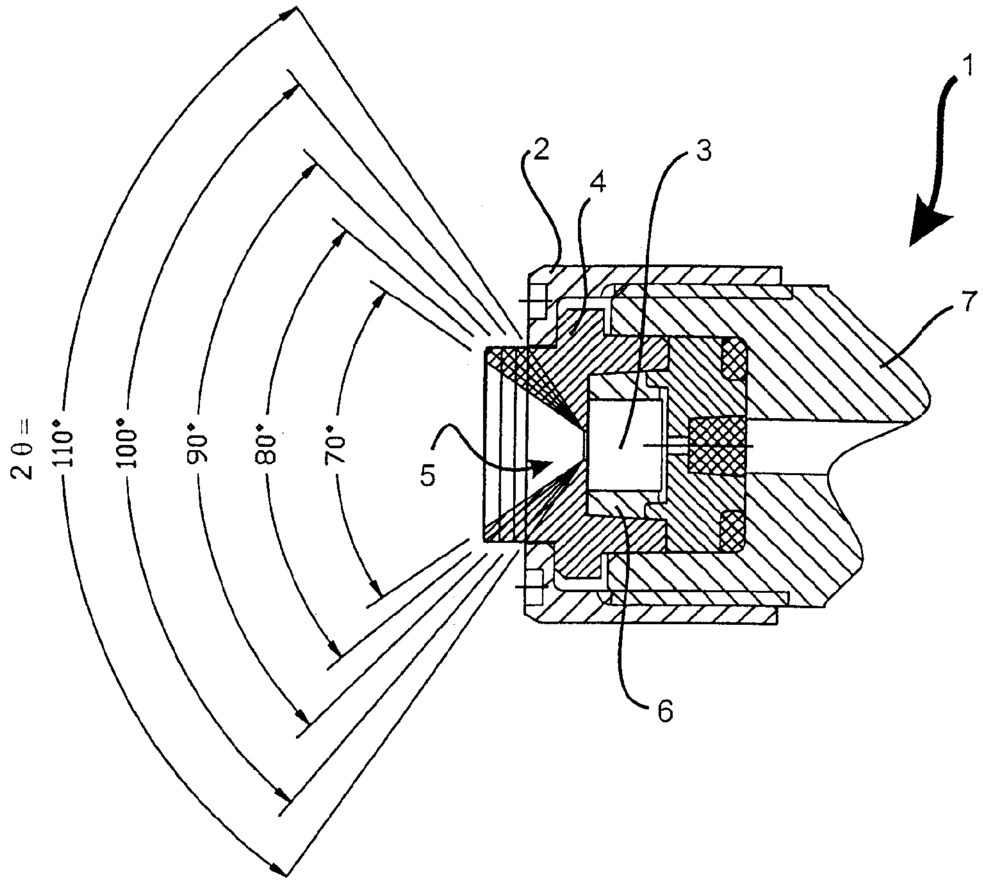
FIG. 7: A view of a first embodiment of a nozzle system in side elevation, partially in section.

FIG. 7 shows a first embodiment of the nozzle system 1 in side elevation, partly in section.

The nozzle 3 or nozzle body as an independent construction unit—so called uniblock—is disposed in a conical sleeve 6 which is in turn placed in the nozzle holder 4. The nozzle holder 4 is clamped to the housing 7 by means of a check nut 2 and this secures the nozzle 3.

At the same time the check nut 2 engages from outside in the nozzle holder 4, although it does not extend into the area in front of the nozzle apertures. The recess 5 is conical in shape, in that it widens out continuously as its distance from the nozzle apertures increases. The recess 5 has a cone angle 20, whilst FIG. 7 shows by way of example a plurality of different cone angles, with the result that this Figure shows five different embodiments of the recess 5 and hence of the nozzle system 1, all basically the same. Specifically, it shows cone angles 2θ of 70 degrees, 80 degrees, 90 degrees, 100 degrees and 110 degrees.

Because the check nut 2 engages in the nozzle holder 4 from outside, the recess 5 is formed exclusively by the nozzle holder 4.

Figure 8:
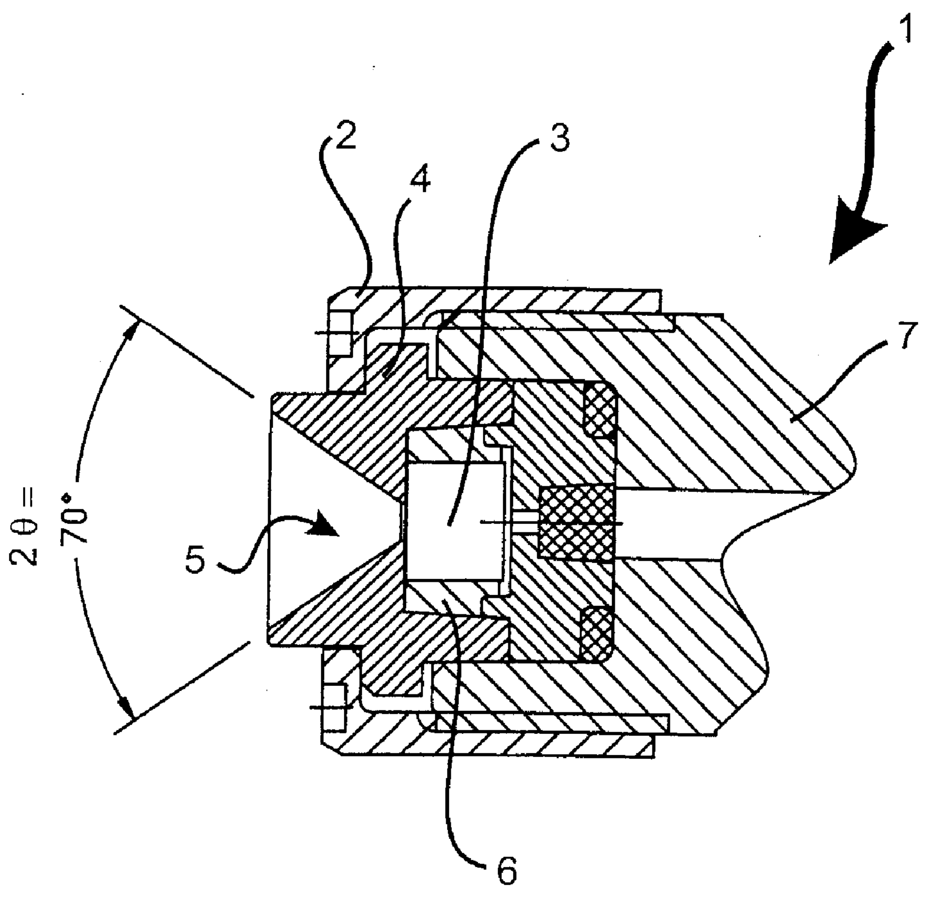
FIG. 8: A view of a second embodiment of a nozzle system in side elevation, partly in section.
Figure 9:
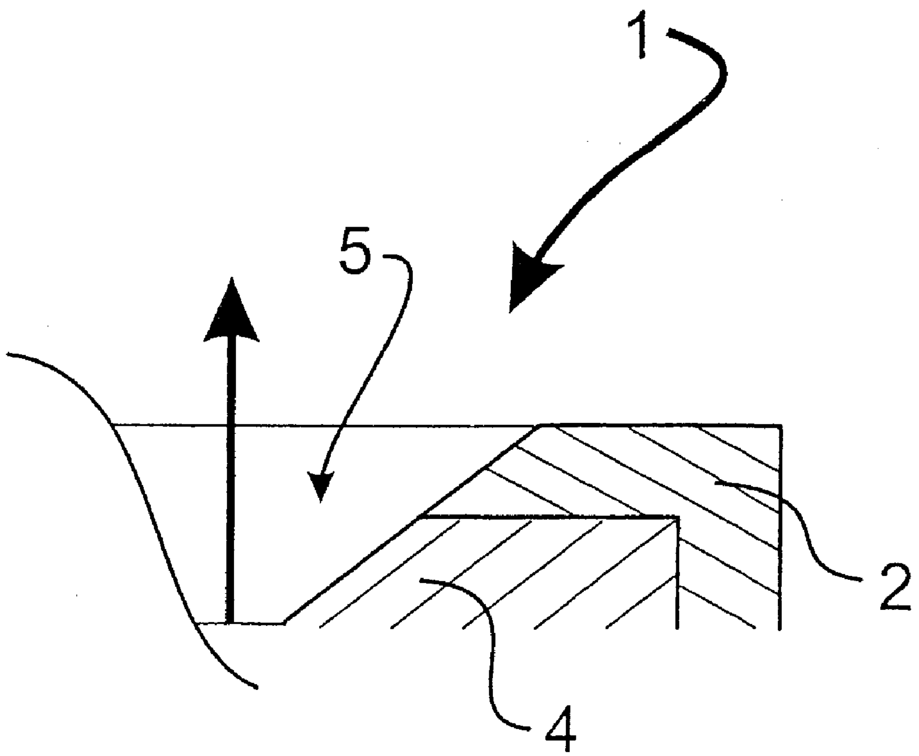
FIG. 9: A diagrammatic view of a nozzle system according to the invention in side elevation, in section.

In contrast, FIG. 8 shows a second embodiment, again in side elevation and partly in section, wherein both the nozzle holder 4 and the check nut 2 extend into the area in front of the nozzle apertures. Otherwise, the nozzle system 1 shown in FIG. 8 corresponds to the nozzle system described above. The same reference numerals have been used for corresponding components, and therefore we refer to the description of FIG. 7 with regard to the components of similar construction.

FIG. 9 again shows a nozzle system 1 according to the invention. This comprises a recess 5 of conical shape. Unlike nozzle systems with a discontinuously expanding recess, the recess 5 does not contain any steps. Such steps may occur in particular in the area where the check nut engages in the nozzle holder. In such cases, particles of the spray mist may accumulate on the edges of the step and thus contribute to the mouthpiece fraction.

Figure 10:
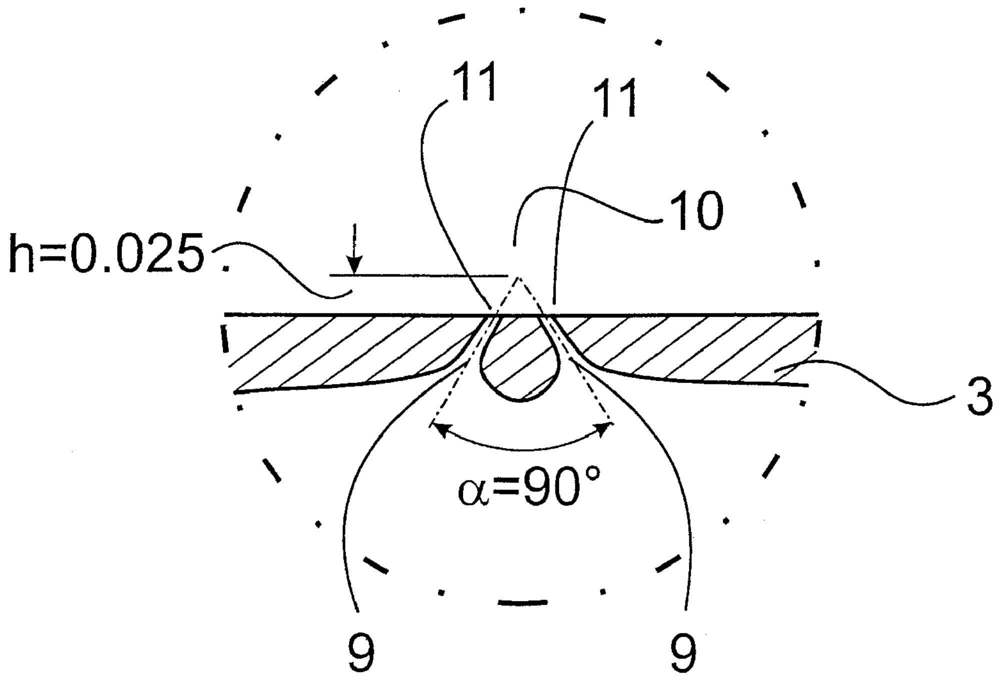
FIG. 10: A diagrammatic view of an embodiment of a nozzle member in side elevation, in section, FIGS. 11*a/b*: Diagram of the Respimat™ type nebulizer.

FIG. 10 is a diagrammatic view of a detail of an embodiment of a nozzle member 3 shown in sectional side view.

The two nozzle channels 9 are arranged so that the jets leaving the nozzle apertures 11 of the nozzle channels meet at the point of collision 10 at an angle $\alpha$=90 degrees. The point of collision 10 has a height of impact h=25 um above the nozzle apertures.

Figure 11A:
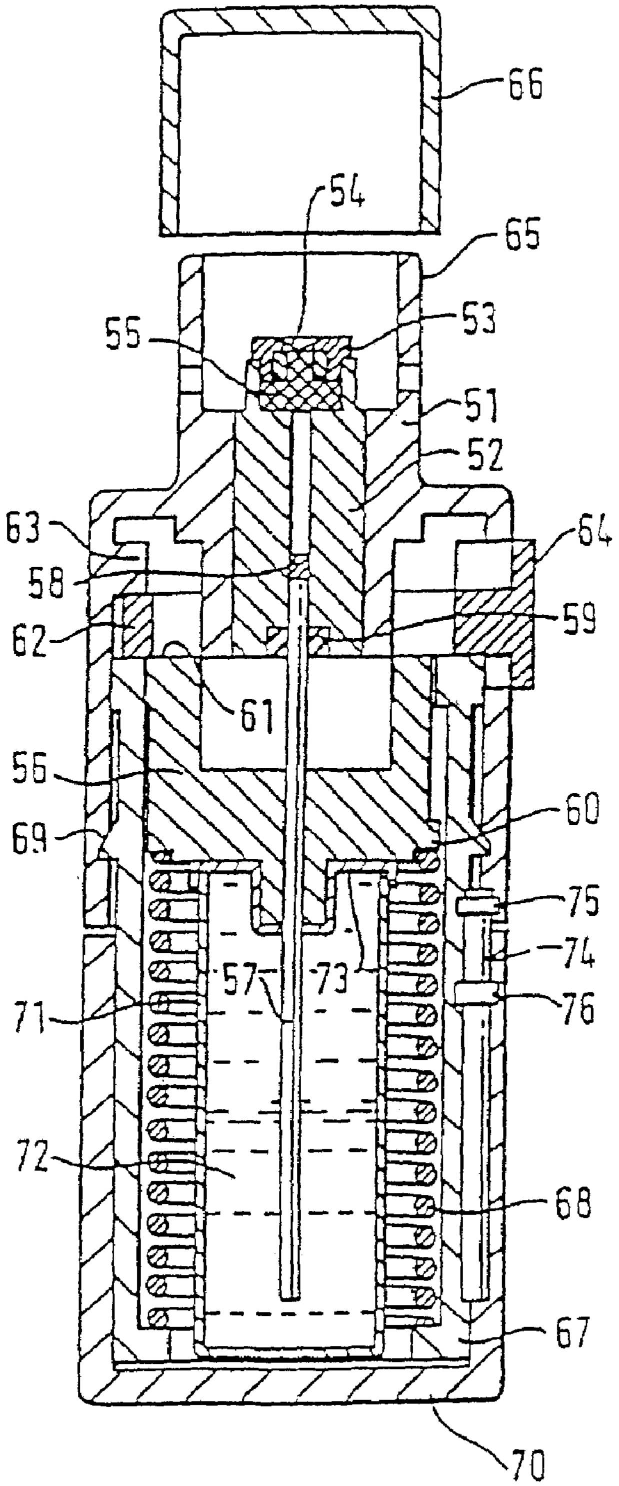
Figure 11B:
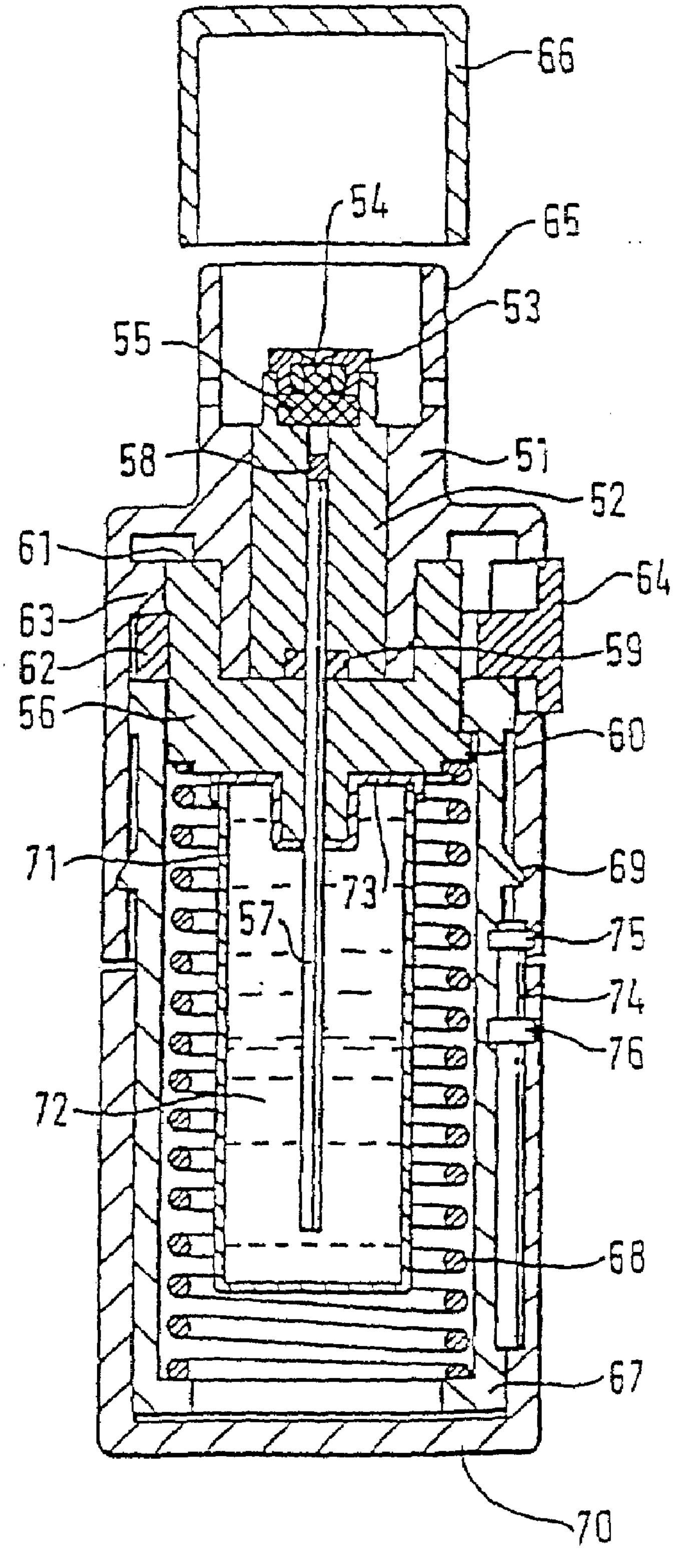

FIG. 11*a* shows a longitudinal section through the atomizer with the spring under tension, FIG. 11*b* shows a longitudinal section through the atomizer with the spring released.

The upper housing part (51) contains the pump housing (52), on the end of which is mounted the holder (53) for the atomizer nozzle. In the holder is the expanding recess (54) and the nozzle body (55). The hollow piston (57) fixed in the power take-off flange (56) of the locking clamping mechanism projects partly into the cylinder of the pump housing. At its end the hollow piston carries the valve body (58). The hollow piston is sealed off by the gasket (59). Inside the upper housing part is the stop (60) on which the power take-off flange rests when the spring is relaxed. Located on the power take-off flange is the stop (61) on which the power take-off flange rests when the spring is under tension. After the tensioning of the spring, the locking member (62) slides between the stop (61) and a support (63) in the upper housing part. The actuating button (64) is connected to the locking member. The upper housing part ends in the mouthpiece (65) and is closed off by the removable protective cap (66). The spring housing (67) with compression spring (68) is rotatably mounted on the upper housing part by means of the snap-fit lugs (69) and rotary bearings. The lower housing part (70) is pushed over the spring housing. Inside the spring housing is the replaceable storage container (71) for the fluid (72) which is to be atomized. The storage container is closed off by the stopper (73), through which the hollow piston projects into the storage container and dips its end into the fluid (supply of active substance solution).

The spindle (74) for the mechanical counter (optional) is mounted on the outside of the spring housing. The drive pinion (75) is located at the end of the spindle facing the upper housing part. On the spindle is the slider (76).

The invention claimed is:

1. A nozzle system, comprising:
- a nozzle having at least two nozzle apertures;
- a nozzle holder; and
- a check nut having the nozzle arranged therein and fixing the nozzle in the nozzle holder, wherein:
  - the nozzle apertures or the nozzle channels opening into the nozzle apertures are arranged so that the jets leaving the nozzle apertures are aimed towards one another at an angle $\alpha$,
  - in the assembled state the check nut extends at least partially into the area in front of the nozzle apertures, and
  - in the assembled state the nozzle holder and the check nut have an inner recess, which begins on the side adjacent to an end face of the nozzle and extends as far as the outside of the nozzle holder parallel to the end face of the nozzle, and which, viewed from the end face of the nozzle, widens out steadily and continuously in the direction of, and as far as, the outside of the check nut parallel to the end face of the nozzle.

2. The nozzle system according to claim 1, characterized in that the recess is funnel-shaped or conical.

3. The nozzle system according to claim 2, characterized in that the recess of conical construction has a cone angle 2θ in the range between 55 degrees and 155 degrees.

4. The nozzle system according to claim 3, characterized in that the recess of conical construction has a cone angle 2θ in the range between 70 degrees and 140 degrees.

5. The nozzle system according to claim 4, characterized in that the recess of conical construction has a cone angle 2θ in the range between 70 degrees and 85 degrees.

6. The nozzle system according to claim 4, characterized in that the recess of conical construction has a cone angle 2θ in the range between 95 degrees and 140 degrees.

7. The nozzle system according to claim 6, characterized in that the recess of conical construction has a cone angle 2θ in the range between 105 degrees and 125 degrees.

8. The nozzle system according to claim 1, characterized in that the point of collision where the jets meet has a height of impact h above the nozzle apertures which is in the range between 20 um and 85 um.

9. The nozzle system according to claim 8, characterized in that the point of collision where the jets meet has a height of impact h above the nozzle apertures which is in the range between 25 um and 75 um.

10. The nozzle system according to claim 9, characterized in that the point of collision where the jets meet has a height of impact h above the nozzle apertures which is in the range between 35 um and 75 um.

11. The nozzle system according to claim 1, characterized in that the angle $\alpha$ is in the range between 50 degrees and 110 degrees.

12. The nozzle system according to claim 11, characterized in that the angle $\alpha$ is in the range between 65 degrees and 95 degrees.

13. The nozzle system according to claim 12, characterized in that the angle $\alpha$ is in the range between 75 degrees and 90 degrees.

14. The nozzle system according to claim 1, characterized in that the spacing a of the nozzle apertures is in the range between 40 um and 125 um.

15. The nozzle system according to claim 14, characterized in that the spacing a of the nozzle apertures is in the range between 50 um and 115 um.

16. The nozzle system according to claim 14, characterized in that the spacing a of the nozzle apertures is in the range between 60 um and 105 um.

17. The nozzle system according to claim 1, characterized in that the nozzle is formed from at least two construction units.

18. A delivery device for liquids, characterized in that it comprises a nozzle system according to one of claim 1.

19. A delivery device according to claim 1, characterized in that it is an atomizer for pharmaceutical liquids.

20. A nozzle system, comprising:
- a nozzle having at least two nozzle apertures, the nozzle being formed from at least two superimposed plates, at least one of the plates having a second microstructure so that the plates lying one on top of the other define, on one side, a liquid inlet connected to a channel system and/or a filter system which then opens into one or more liquid outlets;
- a nozzle holder; and
- a check nut having the nozzle arranged therein and fixing the nozzle in the nozzle holder, wherein:
  - the nozzle apertures or the nozzle channels opening into the nozzle apertures are arranged so that the jets leaving the nozzle apertures are aimed towards one another at an angle $\alpha$,
  - in the assembled state the check nut extends at least partially into the area in front of the nozzle apertures, and
  - in the assembled state the nozzle holder and the check nut have an inner recess, which begins on the side adjacent to an end face of the nozzle and extends as far as the outside of the nozzle holder parallel to the end face of the nozzle, and which, viewed from the end face of the nozzle, widens out steadily and continuously in the direction of, and as far as, the outside of the check nut parallel to the end face of the nozzle.

21. A delivery device for liquids, comprising:
- a lower and an upper housing part mounted to be rotatable relative to one another, the upper part of the housing containing a spring housing with spring which is tensioned by rotating the two housing parts by means of a locking clamping mechanism preferably in the form of a screw thread or gear and is released by pressing a release button on the upper part of the housing, the spring meanwhile moving a power take-off flange connected to a hollow piston on the lower end of which a container can be fitted and at the upper end of which are found a valve and a pressure chamber which is connected for fluid transmission to the nozzle or the nozzle system formed in the upwardly open part of the upper housing part, the nozzle having at least two nozzle apertures;

a nozzle holder; and a check nut having the nozzle arranged therein and fixing the nozzle in the nozzle holder, wherein:

the nozzle apertures or the nozzle channels opening into the nozzle apertures are arranged so that the jets leaving the nozzle apertures are aimed towards one another at an angle α, in the assembled state the check nut extends at least partially into the area in front of the nozzle apertures, and in the assembled state the nozzle holder and the check nut have an inner recess, which begins on the side adjacent to an end face of the nozzle and extends as far as the outside of the nozzle holder parallel to the end face of the nozzle, and which, viewed from the end face of the nozzle, widens out steadily and continuously in the direction of, and as far as, the outside of the check nut parallel to the end face of the nozzle.

22. The delivery device according to claim 21, characterized in that the device is an inhaler or some other atomizer for medicinal liquids.

* * * * *